United States Patent [19]

Zenk et al.

[11] Patent Number: 5,451,649
[45] Date of Patent: Sep. 19, 1995

[54] ORGANOMETALLIC FLUORENYL COMPOUNDS, PREPARATION, AND USE

[75] Inventors: Roland Zenk; Helmut G. Alt, both of Bayreuth, Germany; M. Bruce Welch, Bartlesville, Okla.

[73] Assignee: Phillips Petroleum Company, Bartlesville, Okla.

[21] Appl. No.: 214,934

[22] Filed: Mar. 17, 1994

Related U.S. Application Data

[63] Continuation-in-part of Ser. No. 192,223, Feb. 3, 1994, and a continuation-in-part of Ser. No. 3,221, Jan. 7, 1993, Pat. No. 5,406,013, and a continuation-in-part of Ser. No. 64,630, May 20, 1993, Pat. No. 5,401,817, and a continuation-in-part of Ser. No. 984,054, Nov. 30, 1992, Pat. No. 5,393,911, which is a continuation-in-part of Ser. No. 697,363, May 9, 1991, Pat. No. 5,191,132, said Ser. No. 192,223, is a continuation-in-part of Ser. No. 734,853, Jul. 23, 1991, which is a continuation-in-part of Ser. No. 697,363, Jul. 23, 1991, said Ser. No. 3,221, is a continuation of Ser. No. 697,363, Jul. 23, 1991, said Ser. No. 64,630, is a continuation-in-part of Ser. No. 734,853, Jul. 23, 1991.

[51] Int. Cl.$^6$ .......................... C08F 4/64; C07F 17/00
[52] U.S. Cl. ......................... 526/160; 526/127; 526/351; 526/352; 502/103; 502/117; 502/152; 502/155; 556/1; 556/7; 556/11; 556/19; 556/27; 556/32; 556/43; 556/53; 556/58

[58] Field of Search ............... 526/160, 351, 352, 127; 556/87, 43, 53, 58, 1, 11, 7, 19, 27, 32; 502/103, 117, 152, 155

[56] References Cited

U.S. PATENT DOCUMENTS 3,615,412 10/1971 Hessel ........................... 96/1.5
5,191,132 3/1993 Patsidis et al. .................. 585/375

FOREIGN PATENT DOCUMENTS 2084017 5/1993 Canada .
524624 1/1993 European Pat. Off. .

OTHER PUBLICATIONS

*Makromol. Chem., Marcomol. Symp.* 48/49, 253–295 (1991).
*J. Organomet. Chem.* 435, 299–310 (1992).
CA:114:165103w.

*Primary Examiner*—Fred Teskin
*Attorney, Agent, or Firm*—Edward L. Bowman

[57] ABSTRACT

Benzofluorenyl-containing metallocenes are disclosed along with methods for making the metallocenes. Also disclosed are methods for using the metallocenes as polymerization catalysts. In addition, polymers resulting from such polymerizations are disclosed.

38 Claims, No Drawings

ORGANOMETALLIC FLUORENYL COMPOUNDS, PREPARATION, AND USE

This application is a continuation-in-part of U.S. patent application Ser. No. 08/192,223 filed Feb. 3, 1994, which application was a continuation in part of U.S. patent application Ser. No. 07/734,853 filed Jul. 23, 1991 as a continuation-in-part of U.S. patent application Ser. No. 07/697,363 filed May 9, 1991, now U.S. Pat. No. 5,191,132. This application is also a continuation-in-part of U.S. patent application Ser. No. 08/003,221 filed Jan. 7, 1993 now U.S. Pat. No. 5,406,013 which was a continuation of the same U.S. patent application Ser. No. 07/697,363 filed May 9, 1991. This application is also a continuation-in-part of U.S. patent application Ser. No. 08/064,630 filed May 20, 1993 now U.S. Pat. No. 5,401,817 as a continuation-in-part of the aforementioned U.S. patent application Ser. No. 07/734,853 filed Jul. 23, 1991. This application is further a continuation-in-part of U.S. patent application Ser. No. 07/984,054 filed Nov. 30, 1992 now U.S. Pat. No. 5,393,911 as a continuation-in-part of the aforementioned U.S. patent application Ser. No. 07/697,363 filed May 9, 1991. The disclosures of the above-mentioned applications are incorporated herein by reference.

This invention relates to organometallic compounds. More specifically, this invention relates to organometallic compounds containing at least one benzofluorenyl ligand. In another aspect, this invention relates to polymerization catalyst systems which contain organometallic benzofluorenyl compounds. In still another aspect, this invention relates to a method for polymerizing olefins using such organometallic benzofluorenyl compounds and to the polymers resulting from such polymerizations.

BACKGROUND OF THE INVENTION

Since the discovery of ferrocene in 1951, a number of metallocenes have been prepared by the combination of compounds having cyclopentadienyl structure with various transition metals. The term "cyclopentadienyl structure" as used herein refers to the following structure.

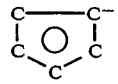

The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydroindene. Thus polycyclic cyclopentadiene compounds are included within the term.

Many cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size of and substitutions on cyclopentadienyl-type ligands has been found to affect the activity of the catalyst, the stereo selectivity of the catalyst, the stability of the catalyst, and other properties of the resulting polymer; however, the effects of various substituents is still largely an empirical matter, that is, experiments must be conducted in order to determine just what effect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

While there are references in the prior art which have envisioned metallocenes containing fluorenyl groups, only a very limited number of fluorenyl-containing metallocenes have actually been prepared prior to the present invention. The Journal of Organometallic Chemistry, Vol. 113, pages 331–339 (1976), the disclosure of which is incorporated herein by reference, discloses preparing bis-fluorenyl zirconium dichloride and bis-fluorenyl zirconium dimethyl. U.S. Pat. No. 4,892,851 and the New Journal of Chemistry, Vol. 14, pages 499–503, dated 1990, the disclosures of which are incorporated herein by reference, each disclose preparing a metallocene from the ligand 1-(cyclopentadienyl)-1-(fluorenyl)-1, 1-dimethylmethylene. The New Journal of Chemistry article also discloses preparing a similar compound in which the cyclopentadienyl radical has a methyl substituent in the number 3 position. The term fluorenyl as used herein refers to 9-fluorenyl unless indicated otherwise.

An object of the present invention is to provide certain new benzofluorenyl-containing metallocenes. Another object of the present invention is to provide a method for preparing new benzofluorenyl-type metallocenes. Still another object of the present invention is to provide polymerization catalysts employing benzofluorenyl-type metallocenes. Still yet another object of the present invention is to provide processes for the polymerization of olefins using benzofluorenyl-type metallocene catalyst systems. Still yet another object of the present invention is to provide polymers produced using such benzofluorenyl-containing metallocene catalysts.

SUMMARY OF THE INVENTION

In accordance with the present invention, there are provided new metallocenes of the formula $R''_x(FlR_n)(CpR_m)MeQ_k$ wherein Fl is a fluorenyl radical; Cp is a cyclopentadienyl, indenyl, tetrahydro indenyl, or fluorenyl radical; each R is the same or different and is a halide or an organo radical having 1 to 20 carbon atoms; R" is a structural bridge linking $(FlR_n)$ and $(CpR_m)$; Me is metal selected from the group consisting of IVB, VB, and VIB metals of the Periodic Table; each Q is the same or different and is selected from the group consisting of hydrocarbyl or hydrocarbyloxy radicals having 1 to 20 carbon atoms, hydrogen, and halogens, x is 1 or 0, k is a number sufficient to fill out the remaining valences of Me, n is a number in the range of 2 to 7, m is a number in the range of 0 to 7, further characterized by the fact that in (FlRn) two adjacent positions are substituted by four connected carbons to form a benzo substituent on the fluorenyl radical.

In accordance with another aspect of the present invention, there is provided a method for forming benzofluorenyl-containing metallocenes comprising reacting an alkali metal salt of the selected benzofluorenyl compound with a transition metal compound of the formula MeQk in the presence of a non-halogenated solvent for the benzofluorenyl salt which solvent is non-coordinating with respect to the transition metal compound.

In accordance with still another aspect of the present invention, there is provided a process for the polymerization of olefins comprising containing said olefins under suitable reaction conditions with a catalyst system comprising a benzofluorenyl-containing metallocene as described above in combination with a suitable organoaluminum co-catalyst.

Still further in accordance with the present invention there is provided the polymer products resulting from such polymerizations.

DETAILED DESCRIPTION OF THE INVENTION

The novel metallocenes provided in accordance with the present invention fall into two broad general categories. One category involves metallocenes in which a benzofluorenyl radical, either substituted or unsubstituted, is bonded to another cyclopentadienyl-type radical by a bridging structure R'' and both the benzofluorenyl and the cyclopentadienyl radicals of that bridged ligand are bonded to the metal. These metallocenes are referred to herein as bridged metallocenes. The other category deals with metallocenes which are unbridged, that is the benzofluorenyl-containing ligand, either substituted or unsubstituted, and the other cyclopentadienyl-type ligands that are bound to the metal are not bound to each other. These metallocenes are referred to as unbridged metallocenes.

The metal, Me is selected from the group IV, VB, or VIB metals of the Periodic Table. The currently preferred metals include titanium, zirconium, hafnium, chromium, and vanadium. The R'' can be selected from any suitable bridging structure. Typical examples include hydrocarbyl or heteroatom containing alkylene radicals containing 1 to 20 carbon atoms, especially 2 to 20 carbon atoms; germanium; silicon; phosphorus; boron; aluminum; tin; oxygen; nitrogen; and the like. The bridge can even be a cyclic hydrocarbyl structure. Some examples include cyclopentylidene, adamantylidene, cyclohexenylidene, cyclohexylidene, indenylidene, and the like. The R'' bridge when hydrocarbyl can be a hydrocarbyl ethylene radical of the formula

wherein each R' is the same or different and is selected from hydrogen or hydrocarbyl radical; or the divalent methylene radical —CR'$_2$—, wherein each R' is the same or different and is selected from methyl, phenyl and hydrogen radicals; or can be aromatic in nature, such as a phenyl-substituted alkylene. The currently most preferred bridges are hydrocarbyl or heteroatom containing alkylene radicals having 1 to 20 carbon atoms. In an especially preferred embodiment k is equal to the valence of Me minus 2.

The substituents R can be selected from a wide range of substituents. In the preferred embodiments the substituents R are each independently selected from halides or hydrocarbyl radicals having 1 to 20 carbon atoms. In a particularly preferred embodiment, the hydrocarbyl radicals R are alkyl, aryl, or arylalkyl radicals. More preferably the alkyl R radicals have 1 to 5 carbon atoms. As noted above n is at least 2 so that at least two adjacent positions on Fl are connected by four carbons so that there is at least one benzo substituent at the 1,2; 2,3; 3,4; 5,6; 6,7; or 7,8 position of Fl. It is also within the scope of the present invention for (FlRn) to have more than one benzo group and for the benzo group or the benzofluorenyl group to be substituted. The substituents on the benzo group can be the same a R, as defined above,but alkyl, aryl, and alkoxy substituents are particularly preferred.

Each Q is a hydrocarbyl radical such as, for example, aryl, alkyl, alkenyl, alkaryl, or arylalkyl radical having from 1 to 20 carbon atoms, hydrocarbyloxy radicals having 1 to 20 carbon atoms, hydrogen, or halogen. Exemplary Q hydrocarbyl radicals include methyl, ethyl, propyl, butyl, amyl, isoamyl, hexyl, isobutyl, heptyl, octyl, nonyl, decyl, cetyl, 2-ethylehexyl, phenyl, and the like. Exemplary halogen atoms include chlorine, bromine, fluorine, and iodine, and of these halogen atoms, chlorine is currently the most preferred. Exemplary hydrocarboxy radicals include methoxy, ethoxy, propoxy, butoxy, amyloxy, and the like.

Illustrative, but non-limiting examples of unbridged metallocenes falling within the scope of the above formula include bis(3,4-benzofluorenyl) zirconium dichloride, bis(1,2:7,8-dibenzofluorenyl) zirconium dimethyl, bis(2,3-benzofluorenyl) hafnium dichloride, bis(2,3:6,7-dibenzofluorenyl)zirconium dichloride, bis(2,5-dimethyl-7H-benzo (c) fluorenyl) zirconium dichloride, bis(6-isopropyl-11H-benzo (b) fluorenyl) zirconium dichloride, bis(2,3-benzofluorenyl)hafnium dichloride, (cyclopentadienyl)(3,4-benzofluorenyl) zirconium dichloride, (cyclopentadienyl) (2,3:6,7-dibenzofluorenyl)zirconium dichloride, (pentamethyl coclopentadienyl) (2,3:6,7-dibenzofluorenyl) zirconium dichloride; bis(1-cyclopentadienyl)-1,1-(dimethyl)-1-(3,4-benzofluorenyl) methane) zirconium dichloride, and the like.

Illustrative, not non-limiting examples of bridged metallocenes containing bridged benzofluorenyl ligands include for example 1-(cyclopentadienyl)-1-(3,4-benzofluorenyl)-1,1-(dimethyl)-methane zirconium dichloride, 1,2-di(3,4-benzofluorenyl) ethane zirconium dichloride, 1,3-di(3,4-benzofluorenyl) propane zirconium dichloride, 1,2-di(2,3:6,7-dibenzofluorenyl) ethane hafnium dichloride, 1,3-di(2,3-benzofluorenyl) propane hafnium dichloride, 1-(3,4-benzofluorenyl)-2-(methyl)-2-(fluorenyl) ethane zirconium dichloride, dimethylsilyl di(2,3:6,7-dibenzofluorenyl) zirconium dichloride, dimethyl silyl (3,4:5,6-dibenzofluorenyl) (cyclopentadienyl) zirconium dichloride, 1,2-di(2,3-benzofluorenyl)ethane zirconium dichloride, 1,2-di(2,5-dimethyl-7H-benzofluorenyl) ethane hafnium dichloride, 1-(3,4-benzofluorenyl)-1-(cyclopentadienyl) methane zirconium dichloride, 1-(3,4-benzofluorenyl)-1-(cyclopentadienyl) methane hafnium dichloride, 1-(2,7-di-t-buryl-fluorenyl)-1-(2,3:6,7-dibenzofluorenyl) methane zirconium dichloride, 1-(3,4-benzofluorenyl)-2-(cyclopentadienyl ethane zirconium dichloride, 1-(2,3:6,7-dibenzofluorenyl)-2-(3-methylcyclopentadienyl) ethane zirconium dichloride, 1(2,3 benzofluorenyl)-2-(indenyl) ethane zirconium dichloride, 1-(2,3-benzofluorenyl)-2-(indenyl) ethane hafnium dichloride, 1-(2,3-benzofluorenyl)-2-(methyl)-2-(indenyl) ethane zirconium dichloride, bis-(3,4-benzofluorenyl) methane vanadium dichloride, 1,2-di(3,4-benzofluorenyl) ethane vanadium dichloride, 1-(2,3-benzofluorenyl)-2-(methyl)-2-(3-methyl cyclopentadienyl) ethane zirconium dichloride, 1-(2,3-benzofluorenyl)-2-(3,4-benzofluorenyl) ethane zirconium dichloride, (1-(2,7-di-t-butylfluorenyl)-2-(2,3:6,7-dibenzofluorenyl) ethane zirconium dichloride, 1,2-di(2,3:6,7-dibenzofluorenyl) ethane zirconium dichloride, 1,2 di(3,4:5,6-dibenzofluorenyl) ethane zirconium dichloride, 1-(2,3-benzofluorenyl)-1-(cyclopentadienyl)-1,1-(dimethyl) methane zirconium dichloride, 1-(2,7-dimesityfluorenyl)-1-(3,4-benzofluorenyl)-1,1-(dimethyl) methane zirconium dichloride, 1-(3,4-benzofluorenyl)-1-(cyclopentadienyl)-1,1-diphenylmethane zirconium dichloride, 1-(3,4:5,6-dibenzofluorenyl)-1-(cyclopentadienyl)-1,1-dimethyl methane zirconium dichloride, 1-(2,3-benzofluorenyl)-1-(cyclopentadienyl) cyclopentane zirconium dichloride, 1-(3,4-benzofluorenyl)-1-(cyclopentadienyl) indanylidene zirconium dichloride, 1-(2,3-benzofluorenyl)-1-(cyclopentadienyl) cyclopentylidene zirconium dichloride, 1-(2,3-benzofluorenyl)-1-(cyclopentadienyl) methane zirconium dichloride, 1-(1,2-benzofluorenyl)-1-(cyclopentadienyl))-1,1-dimethylmethane zirconium dichloride, and 1-(2,3:6,7-dibenzofluorenyl)-1-(cyclopentadienyl)-1,1-diphenylmethane zirconium dichloride and the like.

A particularly preferred type of metallocenes are bridged metallocenes containing at least one symmetrically substituted fluorenyl radical. The term symmetrically substituted as used herein refers to fluorenyl radicals having substituents on opposite portions of the fluorenyl radical, such as for example 2,7-dialkylfluorenyl; 2,7-dicycloalkenylfluorenyl; 3,6-dialkylfluorenyl; 2,7-dihalo fluorenyl; 2,7-diarylfluorenyl; 1,8-dialkylfluorenyl; 4,5-dialkylfluorenyl; 2,7-diarylakylfluorenyl; 2,3:6,7-dibenzofluorenyl; 3,4:5,6-dibenzofluorenyl; and the like. Most preferably the substituents on the fluorenyl are the same. The currently preferred alkyl substituents have 1 to 20 carbon atoms, more preferably 1 to 6 carbon atoms, and most preferrably 1 to 4 carbon atoms. The currently most preferred halide substituents are chloride, iodide, and bromide. Examples of aryl substituents include those having 6 to 20 carbon atoms, with those having 6 to 10 carbon atoms generally more preferred. Likewise the arylalkyl substituents can contain 7 to 20 carbon atoms, more commonly 7 to 10 carbon atoms. It should be recognized that in certain instances if the bridge and the substituents on the (Fln) and/or (Cpm) are particularly bulky it may be difficult to prepare the ligand, the dialkali metal salt, or the metallocene.

The invention metallocenes as well as related metallocenes can be prepared by reacting an alkali metal salt of the selected benzofluorenyl compounds with a suitable transition metal compound in a suitable solvent under suitable reaction conditions.

The bridged benzofluorenyl ligands can be prepared using procedures of the type taught in U.S. Pat. No. 5,191,132 and the aforementioned U.S. patent application Ser. No. 08/064,630 and 07/984,054. Some methylene bridged benzofluorenyl ligands can be made by using 6 or 6,6 substituted fulvenes. Example of fulvene reactions are disclosed in U.S. Pat. No. 4,892,851 and in *J. Organomet. Chem.* 435, 299–310 (1992). In general the technique involves reacting an alkali metal salt of the selected benzofluorene compound with the selected fulvene type compound.

The 6,6-diphenyl fulvenes can be prepared by reacting a suitable aryl bromide, i.e. phenyl bromide, p-tolyl bromide, p-fluorophenyl bromide, or p-t-butylphenyl bromide, with magnesium to form a Grignard reagent. Then the dropwise addition of methyl formate and subsequent hydrolysis results in the formation of the diarylcarbinol. The diarylcarbinol can then be oxidized smoothly to give the corresponding substituted benzophenone, preferably using sulfuric acid and chromic acid. The resulting substituted benzophenone can then be reacted with cyclopentadiene in ethanol containing sodium ethoxide to yield the 6,6-substituted fulvene.

A variation of this technique involves the producting of indanyl fulvene (which can also be called indanylidene fulvene) by reacting 1-indanone with cyclopentadiene in the presence of ethanol and sodium ethoxide. The indanyl fulvene is particularly useful in that it can be reacted with the alkali metal salt of a fluorene compound, i.e. a benzofluorene, to yield an indanyl bridged fluorenyl cyclopentadienyl compound. An example would be 1-(3,4 benzofluorenyl)-1-(cyclopentadienyl) indanylidene.

The benzofluorenyl compounds needed to make the ligands can be prepared using procedures generally known in the prior art. See for example U.S. Pat. No. 3,615,412. Some particularly desirable techniques for forming certain of the benzofluorenyl compounds will be described in further detail in what follows.

The term transition metal compound as used herein includes compounds of the formula MeQk wherein Me, Q, and k are as defined above. Some non-limiting examples include zirconium tetrachloride, hafnium tetrachloride, titanium tetrachloride, cyclopentadienyl zirconium trichloride, fluorenyl cyclopentadienyl zirconium dichloride, 3-methylcyclopentadienyl zirconium trichloride, indenyl cyclopentadienyl zirconium dichloride, 4-methyl fluorenyl zirconium trichloride, pentamethylcyclopentadienyl zirconium trichloride, and the like.

Inventive metallocenes in which Q is hydrocarbyl or hydrocarbyloxy can be readily prepared by reacting the halide form of the metallocene with an alkali metal salt of the hydrocarbyl or hydrocarbyloxy radical under conditions as have been used in the past for forming such ligands in prior art metallocenes. See, for example, the aforemention J. Organomet. Chem. 113, 331–339 (1976). Another approach involves reacting a compound of the formula MeQ$_k$ wherein at least one Q is hydrocarbyl or hydrocarbyloxy with the alkali metal salt of the bridged or unbridged benzofluorenyl compound.

One embodiment of the present invention involves carrying out the reaction of the benzofluorenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes and in a more stable form; and also often allows the reaction to be conducted under higher temperature conditions, than when dichloromethane is used as the diluent. In an especially preferred embodiment the benzofluorenyl-containing salt used as a ligand is also prepared in a liquid diluent that is non-halogenated and non-coordinating toward the transition metal.

The formation of the alkali metal salt of the bridged or unbridged benzofluorenyl compound can be formed using generally any technique known in the art. For example, such can be prepared by reacting an alkali metal alkyl with the cyclopentadienyl type compounds or the bridged compounds having two cyclopentadienyl-type radicals per molecule. The molar ratio of the alkali metal alkyl to the cyclopentadienyl type radicals present can vary, generally however, the ratio would be in the range of about to about , still more preferably about 1/1. Typically, the alkali metal of the alkali metal alkyl would be selected from sodium, potassium, and lithium, and the alkyl group would have 1 to 8 carbon atoms, more preferably 1 to 4 carbon atoms. Preferably, if the benzofluorenyl salt is formed using tetrahydrofuran (THF) as the liquid solvent, the salt is isolated and substantially all of the THF is removed before the salt is contacted with the transition metal halide.

The molar ratio of the bridged or unbridged benzofluorenyl alkali metal compound to the transition metal compound can vary over a wide range depending upon the results desired. Typically, however, when an unbridged benzofluorenyl alkali metal compound is used, the molar ratio of the unbridged benzofluorenyl compound to the transition metal compound is in the range of from about 1 to 1 to about 2 to 1 and when a bridged benzofluorenyl alkali metal compound is used the molar ratio of the bridged benzofluorenyl alkali metal compound to the transition metal compound is about 1 to 1 when one desires a bridged metallocene and about 2 to 1 when one desires an unbridged metallocene.

The resulting metallocene can be recovered and purified using conventional techniques known in the art such as filtration, extraction, crystallization, and recrystallization. It is generally desirable to recover the metallocene in a form that is free of any substantial amount of by-product impurities. Accordingly, recrystallization and fractional crystallization to obtain relatively pure metallocenes is desirable. Dichloromethane has been found to be particularly useful for such recrystallizations. As a general rule, it has been found that the metallocenes based on unbridged fluorenyl compounds are less stable than the metallocene compounds formed from bridged fluorenyl compounds. Since the stability of the various metallocenes varies, it is generally desirable to use the metallocenes soon after their preparation or at least to store the metallocene under conditions favoring their stability. For example the metallocenes can generally be stored at low temperature, i.e. below 0° C. in the absence of oxygen or water.

The resulting benzofluorenyl-containing metallocenes can be used in combination with a suitable co-catalyst for the polymerization of olefins. In such processes the metallocene or the co-catalyst can be employed on a solid insoluble particulate support.

Examples of suitable co-catalysts include generally any of those organometallic co-catalysts which have in the past been employed in conjunction with transition metal-containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride, and the like. Other examples of known cocatalysts include the use of a stable non-coordinating counter anion techniques such as disclosed in U.S. Pat. No. 5,155,080, e.g. using triphenyl carbenium tetrakis(pentafluorophenyl)boronate. Another example would be the use a a mixture of trimethylaluminum and dimethylfluoraluminum such as disclosed by Zambelli et, *Macromolecules*, 22, 2186 (1989). In such processes the metallocene or the co-catalyst can be employed on a solid insoluble support.

The currently most preferred co-catalyst is an aluminoxane. Such compounds include those oligomeric or polymeric compounds having repeating units of the formula

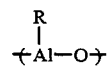

where R is an alkyl group generally having 1 to 5 carbon atoms. Aluminoxanes, also sometimes referred to as poly(hydrocarbyl aluminum oxides) are well known in the art and are generally prepared by reacting an organo aluminum compound with water. Such preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly (ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with the aluminoxane co-catalyst can be used to polymerize olefins. Generally such polymerizations would be carried out in a homogeneous system in which the catalyst and co-catalyst were soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alphs-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3,4-dimethyl-1-hexene, and the like and mixtures thereof. The catalysts are particularly useful for preparing copolymers of ethylene or propylene and generally a minor amount, i.e. about 20 to 10 mole percent, more commonly about 12 mole percent, still more typically less than about 10 mole percent, of a higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal-based catalyst systems can be employed with the present fluorenyl-containing metallocenes.

Generally the molar ratio of the aluminum in the aluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about $-60°$ C. to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

A further understanding of the present invention, its various aspects, objects and advantages will be provided by the following examples.

In the following examples where information is given about the microstructure of polymers as determined by $^{13}$CNMR, the spectra were taken using standard accepted spectroscopy techniques. The polymer was dissolved in trichlorobenzene and the spectra was taken with respect to an internal standard relative to hexamethylsiloxane which has a known reference point relative to tetramethyl silane. From the observed integrals of the relevant peaks, the details regarding the microstructure are calculated Meso Content = (mm) + ½ (mr)
Racemic Content = (rr) + ½ (mr)
Isotacticity = % (mm)
Heterotacticity = % (mr)
Syndiotacticity = % (rr)

$$\text{Randomness Index} = \frac{(mr)100}{2(m)(r)}$$

$$\text{Average Isotactic Block Length} = 1 + \frac{2(mm)}{(mr)}$$

$$\text{Average Syndiotactic Block Length} = 1 + \frac{2(rr)}{(mr)}$$

For more detail regarding the determination of these values, reference can be made to Chapter 3 of the "Chain Structure and Conformation of Macromolecules" by Frank A. Bovey (Academic Press, 1982).

EXAMPLES

EXAMPLE I

Synthesis of 3,4-benzofluorene

A Gringard solution was prepared in a two liter two-necked flask from 13.6 g of magnesium powder, 1,000 ml of diethylether, and 123 g of distilled 1-bromo-2-methylnapthalene. Then 0.5 g of Ni(TPP)$_2$Cl$_2$ was added and 114 g of iodobenzene was added dropwise with stirring. The light brown suspension became hot and was heated for a further 10 hours under reflux. The resulting reaction product was hydrolyzed and then extracted with ether, dried and freed from the solvent. By vacuum distillation, an orange liquid was obtained which was determined to be 2-methyl-1-phenylnapthalene.

Then 97.8 g of that product was combined with 81.9 g of N-bromosuccinimide and 4.2 g of α,α-azo bis isobutyronitrile in 300 ml of carbon tetrachloride and then heated under reflux for 8 hours. The resulting product is filtered off from the succinimide. Then after the solvent is removed in a vacuum, a pale yellow solid was obtained which was determined to be 2-bromomethyl-1-phenylnapthalene was heated with 23 g of calcium carbonate in a mixture consisting of 250 ml of an equal volume mixture of water and dioxane for 10 hours under reflux. The reaction mixture was carefully poured into diluted hydrochloric acid and then extracted with ether and dried and freed of solvent. The resulting product, 2-hydroxymethyl-1-phenylnaphthalene, in an amount of about 0.45 mol was dissolved in 200 ml of acetone and added dropwise to a hot suspension of 207g of KMnO$_4$, 280 ml of water, and 1000 ml of acetone. The suspension was poured into a large glass beaker containing 1000 ml of water to dissolve the magnesium dioxide by the portion-wise addition of dilute HCl and Na$_2$SO$_3$. The product 1-phenylnaphthalene-2-carboxylic acid was isolated by extraction with ether together with extraction of the organic phase with aqueous carbonate solution. This carboxylic acid product was then reacted with polyphosphoric acid. Specifically, 250 g of polyphorphoric acid was heated to 100°–120° C. in a 1000 ml flask. Then 23.9 g of the 1-phenylnaphthalene-2-carboxylic acid was added in portions and the mixture allowed to stand for 1 hour at that temperature. The mixture was then allowed to cool and diluted to 750 ml by the careful addition of ice water. The sticky crude product was extracted with hot toluene and washed with warm aqueous sodium bicarbonate solution. The organic phase was dried and filtered over silica gel. In a cooling cabinet, dark red crystals of the benzo(c) fluorenone separated from the deep red solution.

9.8 grams of the benzo(c) flurenone were dissolved in 200 ml of terahydrofuran and hydrogenated in the presence of 0.5 g of a palladium carbon catalyst containing 10 wt % palladium under atmospheric pressure and room temperature. The resulting product was dried over Na$_2$SO$_4$, the solvent removed and the residue extracted with pentane and filtered over silica gel. Colorless platelettes of 3,4-benzofluorene, also sometimes referred to as benzo(c) fluorene, were recovered.

EXAMPLE II

Preparation of 1,2-di-(9-(3,4-benzofluorenyl)) ethane and Metallocene 3 grams of 3,4-benzofluorene was dissolved in 100 ml of ether and reacted with 8.7 ml of a 1.6 molar hexane solution of n-butyllithium. Then 0.6 ml of 1,2-dibromoethane was added to the orange solution after 3 hours and then the mixture was stirred for four more hours. Then a little water was added to carry out hydrolysis, the solid product was filtered off, washed with water, and then with ether and pentane and then recrystallized from toluene. A mixture of the rac/meso isomers of bis 1,2-(3,4-benzofluorenyl) ethane was obtained.

The isomeric mixture of the 1,2-ethylene bridged-bis 3,4-benzofluorene ligand was dissolved in diethyl ether and stirred with two molar equivalents of n-butyllithium for at least 8 hours at room temperature then one molar equivalent of zirconium tetrachloride was added. The mixture was stirred for several more hours. The complex was extracted with dichloromethane and filtered over Na₂SO₄. A solid precipitates out at about −25° C. to yield an approximately equal mixture of the rac- and meso-forms of the 1,2-bis-(3,4-benzofluorenyl) ethane zirconium dichloride.

EXAMPLE III

Ethylene Polymerization

Ethylene homopolymerization was carried out using the metallocene of Example II. The polymerization was conducted in a 1-liter autoclave using 0.04 mg of the 1,2-di-(9-(3,4-benzofluorenyl)) ethane zirconium dichloride in 300 ml of hexane with 1 ml of a 30 wt % toluene solution of methylaluminoxane. After this, an ethylene pressure of 10 bar was applied and the reaction mixture stirred for 1 hour at 60° C. The recovered polymer was dried using a vacuum. A yield of 27.3 g of polymer was obtained. This translates to an activity of $4.2 \times 10^5$ g of polyethylene/mol zirconium-hour.

A comparable polymerization was carried out employing the metallocene, 1,2-bis(fluorenyl) ethane zirconium dichloride, and the activity was only $5 \times 10^4$ g polyethylene/mol Z-Hr. It is theorized that perhaps the benzo substituents keep the aluminoxane counter ion away from the active site without hindering the monomer from coordination and insertion.

EXAMPLE IV 1-(3,4-benzofluorenyl)-1,1-dimethyl-1-(cyclopentadienyl) methane zirconium dichloride A metallocene was prepared by dissolving 5 g of 3,4-benzofluorene in 100 ml of ether and then a molar equivalent of n-butyllithium in hexane was slowly added. The liquid was then stirred for several hours at room temperature. Then a molar equivalent quantity of 6,6-dimethylfulvene was added and stirring was continued at room temperature. Decoloration of the solution occurred quickly. Then approximately 1 molar equivalent of n-butyllithium was added in order to transform any possible excess fulvene into a readily soluble colorless derivative. The mixture was then stirred for further 30 minutes and then hydrolyzed with a little water. The resulting dimethylmethylene-bridged ligand was then isolated and purified by dissolving in a solvent, filtering over silica gel and crystallization.

The 1 g of the bridged benzofluorenyl ligand was added to 30 ml of diethylether and stirred with exactly 2 molar equivalents of n-butyllithium for about 8 hours at room temperature. After the liquid became well colored, 1 molar equivalent of zirconium tetrachloride was added and the mixture was stirred for several more hours. The resulting metallocene was then recovered and purified.

EXAMPLE V 1-(3,4 benzofluorenyl)-1,1 diphenyl-1-(cyclopentadienyl) methane zirconium dichloride 1-(3,4 benzofluorenyl)-1,1-diphenyl-1-(cyclopentadienyl) methane was prepared using a procedure similar to that used in Example IV but starting with 6,6-diphenylfulvene. In this preparation it was necessary to stir the reaction mixture overnight to obtain the desired degree of reaction.

The resulting diphenylmethane bridged benzofluorenyl ligand was then reacted with zirconium tetrachloride in the same manner as used in Example IV.

EXAMPLE VI

Propylene Polymerization

The dimethyl methane bridged benzofluorenyl metallocene of Example IV was evaluated for the polymerization of propylene. Polymerization grade propylene was condensed into a 1-liter autoclave reactor. It was stirred for 15-30 min with 10 ml of a 30 wt % methylaluminoxane solution at 20° C. and then cooled down to a temperature in the range of 0 to −2° C. A catalyst solution was prepared by combining the metallocene of Example IV with 1 ml of a 30 wt % solution of methylaluminoxane in toluene. The catalyst solution was forced into the cool stirred autoclave using argon pressure. The temperature was then brought to 60° C. and maintained at that temperature for 120 min and then the polymerization was terminated by draining the unconsumed propylene. The polymerization demonstrated an activity of $34.9 \times 10^3$ kg of polypropylene per mol Zr-hr. The polymer had a nominal molecular weight of $37.5 \times 10^3$ g/mol. This was determined using a precision capillary viscometer in decalin at 135° C. For the determination, calibration curves were available for three different polymer concentrations. From carbon $^{13}$NMR it was determined that the polymer had a racemic content of 93.7, i.e. it would be viewed as a syndiotactic polymer.

EXAMPLE VII

Bulk polymerization of propylene using the diphenyl methane bridged benzofluorenyl metallocene of Example V was carried out using the same technique as described in Example VI. This polymerization demonstrated an activity of $42.9 \times 10^3$ kilograms of polypropylene/mol Zr-hr. The nominal molecular weight was $330 \times 10^3$ grams/mol. The presence of the phenyl groups appears to be effective in increasing the molecular weight of the polymer without causing any significant reduction in the activity of the catalyst.

EXAMPLE VII

Propylene polymerization using the metallocene of Example II, i.e. the bis(benzofluorenyl) ethylene bridged zirconium dichloride, was carried out using conditions substantially the same as those used in Example VI and VII. The resulting polypropylene had an isotacticity of 34.3%, a heterotacticity of 39.7%, and a syndiotacticity of 25.9% as determined by carbon $^{13}$NMR. The polymer had a metal flow of 204. The molecular weight as determined by size exclusion chromatography was 39,000. The nominal molecular weight was 5,000.

That which is claimed is:

1. A metallocene of the formula $Rx''(FlR_n)(CpR_m)MeQ_k$ wherein Fl is a fluorenyl radical, Cp is a cyclopentadienyl, indenyl, tetrahydroindenyl, or fluorenyl radical, each R is the same or different and is a halide or an organo radical having 1 to 20 carbon atoms, R" is a structural bridge linking $(FlR_n)$ and $(CpR_m)$, Me is metal selected from the group consisting of IVB, VB, and VIB metals of the Periodic Table, each Q is the same or different and is selected from the group consisting of hydrocarbyl or hydrocarbyloxy radicals having 1 to 20 carbon atoms, hydrogen, and halogen, x is 0 or 1, k is a number sufficient to fill out the remaining valences of Me, n is a number in the range of 2 to 7, m is a number in the range of 0 to 7, further characterized by the fact that in (FlR$_n$) two adjacent positions are substituted by four connected carbons to form at least one benzo substituent.

2. A metallocene according to claim 1 wherein (FlR$_n$) is selected from the group consisting of, substituted or unsubstituted, 2,3-benzofluorenyl; 3,4-benzofluorenyl; 1,2-benzofluorenyl; 1,2:5,6-dibenzofluorenyl; 2,3:6,7-dibenzofluorenyl; 3,4:5,6-dibenzofluorenyl, and 1,2:7,8-dibenzofluorenyl radicals.

3. A metallocene according to claim 2 wherein (CpR$_m$) is an unsubstituted cyclopentadienyl radical.

4. A metallocene according to claim 2 wherein (CpR$_m$) and (FlR$_n$) are structurally different.

5. A metallocene according to claim 2 wherein n is greater than 2.

6. A metallocene according to claim 2 wherein m is a number in the range of 1 to 4.

7. A metallocene according to claim 2 wherein Me is selected from Ti, Zr, and Hf.

8. A metallocene according to claim 2 wherein Me is selected from Zr and Hf.

9. A metallocene according to claim 7 wherein Cp is selected from the group consisting of cyclopentadienyl and indenyl radicals.

10. A metallocene according to claim 2 wherein x is 1.

11. A metallocene according to claim 10 wherein (FlR$_n$) is selected from 3,4-benzofluorenyl; 2,3:6,7-dibenzofluorenyl; and 2,3-benzofluorenyl.

12. A metallocene according to claim 10 selected from the group consisting of:
(1-(3,4-benzofluorenyl)-1-cyclopentadienyl-1,1-(dimethyl) methane) zirconium dichloride; (1-(2,3:6,7-dibenzofluorenyl)-1-cyclopentadienyl-1,1-(dimethyl) methane) zirconium dichloride; (1-(3,4-benzofluorenyl)-1-cyclopentadienyl-1,1-(diphenyl) methane) zirconium dichloride; (1-(2,3-benzofluorenyl)-1-cyclopentadienyl-1,1-(dimethyl) methane) zirconium dichloride; (1-(1,2-benzofluorenyl)-1-cyclopentadienyl-1,1-(dimethyl) methane) zirconium dichloride; (1-(3,4-benzofluorenyl)-1-pentamethyl cyclopentadienyl-1,1-(dimethyl) methane) zirconium dichloride; (1-(2,3:6,7-dibenzofluorenyl)-1-cyclopentadienyl-1,1-(diphenyl) methane) zirconium dichloride; (1-(2,3-benzofluorenyl)-1-cyclopentadienyl-1,1-(diphenyl) methane) zirconium dichloride; (1-(1,2-benzofluorenyl)-1-cyclopentadienyl-1,1-(dimethyl) methane) zirconium dichloride; (1-(3,4-benzofluorenyl)-1-(cyclopentadienyl)-1-(phenyl) methane)zirconium dichloride, 1-(2,5-dimethyl-7 H benzo(c)fluorenyl)-1-(cyclopentadienyl)-1,1-dimethyl methane) zirconium dichloride, 1-(1,2-benzofluorenyl)-1-(cyclopentadienyl)-1-(phenyl) methane) zirconium dichloride, 1-(3,4-benzofluorenyl)-1-(fluorenyl)-1,1-dimethyl methane) zirconium dichloride, 1-(3,4 benzofluorenyl)-1-(indenyl)-1-phenyl methane) zirconium dichloride, 1-(3,4-benzofluorenyl)-1-(cyclopentadienyl)-1-methyl methane) zirconium dichloride, and 1-(2,3:6,7-dibenzofluorenyl)-1-(cyclopentadienyl)cyclopentane) zirconium dichloride.

13. A metallocene according to claim 10 wherein R'' is the divalent methylene radical —CR'$_2$—, wherein each R' is the same or different and selected from the group consisting of methyl, phenyl, and hydrogen radicals, with the further proviso that at least one R' is hydrocarbyl.

14. A metallocene according to claim 13 having the name (1-(3,4-benzofluorenyl)-1-cyclopentadienyl-1,1-(diphenyl) methane) zirconium dichloride.

15. A metallocene according to claim 13 having the name (1-(3,4-benzofluorenyl)-1-cyclopentadienyl-1,1-(dimethyl) methane) zirconium dichloride.

16. A metallocene according to claim 13 having the name (1-(2,3:6,7-dibenzofluorenyl)-1-cyclopentadienyl-1,1-(dimethyl) methane) zirconium dichloride.

17. A metallocene according to claim 13 having the name (1-(3,4:5,6-dibenzofluorenyl)-1-cyclopentadienyl-1,1-(dipenyl) methane) zirconium dichloride.

18. A metallocene according to claim 13 having the name (1-(1,2:5,6-dibenzofluorenyl)-1-cyclopentadienyl-1,1-(dimethyl) methane) zirconium dichloride.

19. A metallocene according to claim 10 wherein R'' is a hydrocarbyl ethylene radical of the formula $$\begin{array}{c} R' \ R' \\ | \ | \\ -C-C- \\ | \ | \\ R' \ R' \end{array}$$

wherein each R' is the same or different and is selected from hydrogen or hydrocarbyl radical.

20. A metallocene according to claim 19 wherein R' is hydrogen.

21. A metallocene according to claim 20 wherein (CpR$_m$) is unsubstituted fluorenyl.

22. A metallocene according to claim 20 wherein (CpR$_m$) and (FlRn) are the same.

23. A metallocene according to claim 22 wherein (FlR$_n$) is selected from unsubstituted 3,4-benzofluorenyl and unsubstituted 3,4:5,6 dibenzofluorenyl.

24. A metallocene according to claim 23 wherein Me is zirconium or hafnium, k is 2, and Q is a halogen.

25. A metallocene according to claim 10 wherein R'' is a hydrocarbyl group containing 2 to 20 carbon atoms, (CpR$_m$) is an unsubstituted cyclopentadienyl radical, and (FlR$_n$) is selected from the group consisting of 3,4-benzofluorenyl; 2,3-benzofluorenyl; and 2,3:6,7-dibenzofluorenyl radicals, each Q is selected from the group consisting of halogen atoms, C1 to C10 alkyl groups and aryl groups, and Me is selected from Ti, Zr, and Hf.

26. A metallocene according to claim 25 wherein R'' is a hydrocarbyl group containing 4 to 20 carbon atoms.

27. A process for polymerizing an olefin comprising contacting said olefin under suitable polymerization conditions with a catalyst system comprising a fluorenyl-containing metallocene as set forth in claim 1 and a suitable cocatalyst.

28. A process according to claim 27 wherein said cocatalyst comprises an alkylaluminoxane.

29. A process according to claim 28 wherein said metallocene is selected from the group consisting of (1-(3,4-benzofluorenyl)-1-(cyclopentadienyl)-1,1-(dimethyl) methane) zirconium dichloride; (1-(2,3-benzofluorenyl)-1-(cyclopentadienyl)-1,1-(dimethyl) methane) zirconium dichloride; (1-(3,4-benzofluorenyl)-1-(cyclopentadienyl)-1,1-(diphenyl) methane) zirconium dichloride; (1-(2,3:6,7 dibenzofluorenyl)-1-cyclopentadienyl-1,1-(dimethyl) methane) zirconium dichloride; (1-(2,3-benzofluorenyl)-1-cyclopentadienyl-1,1-(diphenyl) methane) zirconium dichloride; (1-(2,3:6,7-dibenzofluorenyl)-1-(cyclopentadienyl)-1,1-(diphenyl) methane) zirconium dichloride; (1-(3,4-benzofluorenyl)-1-

(cyclopentadienyl)-1-(phenyl) methane) zirconium dichloride; (1-(3,4-benzofluorenyl)-2-(indenyl) ethane) zirconium dichloride; (1,2-di(3,4:5,6-dibenzofluorenyl) ethane zirconium dichloride; (1,2-di(3,4-benzofluorenyl) ethane) zirconium dichloride; and (1-(3,4-benzofluorenyl)-2-(cyclopentadienyl)-ethane) zirconium dichloride.

30. A process according to claim 28 wherein ethylene is polymerized.

31. A process according to claim 30 wherein ethylene homopolymer is produced.

32. A process according to claim 31 wherein said metallocene consists essentially of an rac/meso mixture of (1,2-di(3,4-benzofluorenyl) ethane) zirconium dichloride.

33. A process according to claim 30 wherein ethylene is polymerized in the presence of another alpha-olefin having 4 to 8 carbon atoms.

34. A process according to claim 28 wherein propylene is polymerized.

35. A process according to claim 34 wherein propylene homopolymer is produced.

36. A process according to claim 35 wherein $FlR_n$ and $CpR_m$ in said metallocene are different and $FlR_n$ is selected from the group consisting of 3,4-benzofluorenyl; 2,3-benzofluorenyl; and 2,3:6,7-dibenzofluorenyl.

37. A process according to claim 35 wherein said metallocene consists essentially of (1-(3,4-benzofluorenyl)-1-cyclopentadienyl-1,1-(diphenyl) methane) zirconium dichloride.

38. A process according to claim 35 said metallocene consists essentially of (1-(3,4-benzofluorenyl)-1-(cyclopentadienyl)-1,1-(dimethyl) methane) zirconium dichloride.

* * * * *